US011519856B2

(12) United States Patent
Thon et al.

(10) Patent No.: US 11,519,856 B2
(45) Date of Patent: Dec. 6, 2022

(54) METHOD FOR OPTICALLY DETECTING BIOMARKERS

(71) Applicant: MECWINS, S.A., Tres Cantos (Madrid) (ES)

(72) Inventors: Andreas Thon, Madrid (ES); Valerio Pini, Madrid (ES); Antonio Salvador-Matar Renteria, Madrid (ES); Virginia Cebrián Hernando, Madrid (ES); Carlos García Aguado, Madrid (ES); Jesús Oscar Ahumada Heredero, Madrid (ES)

(73) Assignee: Mecwins, S.A., Madrid (ES)

( * ) Notice: Subject to any disclaimer, the term of this patent is extended or adjusted under 35 U.S.C. 154(b) by 186 days.

(21) Appl. No.: 16/839,300

(22) Filed: Apr. 3, 2020

(65) Prior Publication Data
US 2020/0319102 A1  Oct. 8, 2020

(30) Foreign Application Priority Data
Apr. 3, 2019  (EP) ..................................... 19382245

(51) Int. Cl.
G01N 21/47  (2006.01)
G01N 21/552  (2014.01)
(Continued)

(52) U.S. Cl.
CPC ............. *G01N 21/47* (2013.01); *G01N 15/06* (2013.01); *G01N 15/1475* (2013.01);
(Continued)

(58) Field of Classification Search
CPC .... G01N 21/47; G01N 15/06; G01N 15/1475; G01N 21/554; G01N 33/54346;
(Continued)

(56) References Cited

U.S. PATENT DOCUMENTS

| 2002/0056808 | A1* | 5/2002 | Tsuneta | ................... | H01J 37/21 |
| | | | | | 250/306 |
| 2003/0139886 | A1* | 7/2003 | Bodzin | .................. | G01N 21/47 |
| | | | | | 702/28 |

(Continued)

FOREIGN PATENT DOCUMENTS

| EP | 3236234 A1 | 10/2017 |
| EP | 3153844 B1 | 5/2018 |

(Continued)

OTHER PUBLICATIONS

European search report for EP19382245.9, dated Aug. 2, 2019, 2 pages.

Primary Examiner — Samuel P Siefke
Assistant Examiner — Henry H Nguyen
(74) Attorney, Agent, or Firm — Danielson Legal LLC

(57) ABSTRACT

A method for optically detecting biomarkers in a biosensor is disclosed, wherein the optical detection obtains spatially and spectrally resolved optical signals from a sample on a biosensor, and one or more of these spatially and spectrally resolved optical signals can be analyzed in parallel with image acquisition. The image analysis comprises reading data of the acquired images, correcting them to reduce inhomogeneities and noise, localizing particles in the images, characterizing each particle individually to obtain its position and characterization parameters, and classifying the particles based on their characterization parameters.

(Continued)

Using the number of particles per class for all the acquired images of the sample, a statistical value is calculated per sample and each statistical value is correlated with an indication of the presence of a biomarker in the sample.

16 Claims, 12 Drawing Sheets

(51) Int. Cl.

| | | |
|---|---|---|
| *G01N 33/543* | (2006.01) | |
| *G06T 5/00* | (2006.01) | |
| *G01N 15/14* | (2006.01) | |
| *G01N 15/06* | (2006.01) | |
| *G01N 21/59* | (2006.01) | |
| *G01N 15/00* | (2006.01) | |
| *G06T 5/40* | (2006.01) | |

(52) U.S. Cl.
CPC ..... *G01N 21/554* (2013.01); *G01N 33/54346* (2013.01); *G06T 5/002* (2013.01); *G06T 5/40* (2013.01); *G01N 2015/0038* (2013.01); *G01N 2021/5903* (2013.01); *G06T 2207/30168* (2013.01)

(58) Field of Classification Search
CPC ... G01N 2015/0038; G01N 2021/5903; G01N 2015/1472; G01N 15/1468; G01N 2015/0693; G06T 5/002; G06T 5/40; G06T 2207/30168; G06T 7/0012; G06T 7/90

See application file for complete search history.

(56) References Cited

U.S. PATENT DOCUMENTS

| | | | |
|---|---|---|---|
| 2004/0126008 A1* | 7/2004 | Chapoulaud | G06K 9/6281 382/128 |
| 2011/0002516 A1* | 1/2011 | Manri | G01N 15/147 382/128 |
| 2011/0090240 A1* | 4/2011 | Cohen | G06T 5/20 345/589 |
| 2014/0177932 A1* | 6/2014 | Milne | G06T 7/60 382/128 |
| 2014/0275947 A1* | 9/2014 | Fonte | A61B 5/026 600/407 |
| 2015/0187074 A1* | 7/2015 | Dommett | G06T 7/0004 348/187 |
| 2015/0346076 A1* | 12/2015 | Stramski | G01N 15/1468 356/336 |
| 2016/0117818 A1* | 4/2016 | Park | A61B 5/7425 382/131 |

FOREIGN PATENT DOCUMENTS

| | | |
|---|---|---|
| WO | 01/84106 A2 | 11/2001 |
| WO | 01/84106 A3 | 11/2001 |
| WO | 2006/084283 A2 | 8/2006 |
| WO | 2006/084283 A3 | 8/2006 |

* cited by examiner

METHOD FOR OPTICALLY DETECTING BIOMARKERS

CROSS-REFERENCE TO RELATED APPLICATIONS

The present application claims the benefit of and priority to European Patent Application No. 19382245.9, filed on Apr. 3, 2019, the entire disclosure of which is incorporated by reference as if set forth in its entirety herein.

FIELD OF THE INVENTION

The present invention has its application within the sector of optical sensors and biosensors, more specifically, based on dark-field micro-spectrophotometry.

More particularly, the present invention refers to a method for the ultra-sensitive and ultra-fast simultaneous optical detection of multiple protein biomarkers.

BACKGROUND OF THE INVENTION

A biosensor measures the physical changes that a biological recognition layer bound to a solid transducer undergoes when it interacts with a sample containing molecular targets.

An example of a biosensing platform is disclosed in EP3153844 and provides an ultra-sensitive detection of protein biomarkers deposited onto a surface. The key features of this biosensing platform are listed below:

1) Each biomarker is labeled with a specific type of plasmonic nanoparticle (nanospheres, nanorods, nanocubes, nanoprisms, etc.)
2) Plasmonic nanoparticles are deposited onto a functionalized suspended multi-dielectric substrate that allows at the same time:
   i. to strongly enhance the weak scattering signal coming from plasmonic nanoparticles (optoplasmonic effect),
   ii. to weigh the mass of the nanoparticles.
3) The biosensing platform presents a dual transduction mechanism:
   a) Optical detection: plasmonic nanoparticles are optically detected with standard dark-field microscopy.
   b) Mechanical detection: the mass of the plasmonic nanoparticles is detected by measuring the change of the resonance frequency of the suspended mechanical substrate after the deposition of the nanoparticles.

The main drawbacks of this biosensing platform disclosed in EP3153844 are that it is not possible: i) to distinguish different types of nanoparticles, because the optical signal is averaged over all the surface area; and ii) to extract fundamental spectral properties of the nanoparticles on the surface, because the optical recognition is performed with standard dark-field microscopy. In the same way, the mechanical transduction cannot yield any information about individual nanoparticles, because in this mode only integral mechanical properties of the sensor are measured.

Therefore, it is highly desirable to provide an optical scanner with a robust and fast method to detect biomarkers in a biosensor and not dependent on the experimental variability observed during the measurement process (inhomogeneity of the sample illumination, variations of the biosensor substrate and variations of the nanoparticles).

SUMMARY OF THE INVENTION

The present invention solves the aforementioned problems and overcomes previously explained state-of-the-art work limitations by providing a method to detect biomarkers optically wherein the optical detection obtains spatially and spectrally resolved optical signals from a sample on a biosensor and wherein one or more of these spatially and spectrally resolved optical signals can be analyzed in parallel with the image acquisition. The analysis of the optical signals provides information (e.g. the presence and or concentration levels) of the biomarkers in each sample, this information containing much more and/or different spectral information than the "typical" microscope images. The main part of the analysis runs in parallel with the image acquisition and multiple images can be analyzed in parallel as a highly efficient image analysis is implemented, which allows the images to be handled independently for most of the analysis and minimizes the time between the image acquisition and the achievement of results.

For the image acquisition, each image is read and, if needed, corrections are applied (background, inhomogeneities etc.). The core of the analysis consists in the recognition, the classification and the counting of particles. To do this, the particles are first localized in the image sample, they are characterized (brightness, emission spectrum etc.), the results are used to classify them (nano-particle monomer, cluster, dust etc.), and finally they are counted per class. These numbers constitute the principal result per image; in addition, further results are derived which allow the control of the measurement quality (correct focusing, etc.). As each specific type of plasmonic nanoparticle is associated specifically with a different biomarker, from the numbers of the different particles in each image sample, the concentrations of the respective biomarkers in the corresponding sample can be deduced.

An aspect of the present invention refers to a method for detecting biomarkers optically, which comprises:
   An image acquisition, performed with an optical scanner, of simultaneously spatially and spectrally resolved images from at least one sample of the biosensor; and
   an image analysis performed in parallel with the image acquisition;
      wherein the image analysis comprises the following steps:
         reading data of the acquired images from storage means;
         correcting the read data to reduce inhomogeneities and noise of the acquired images;
         localizing particles in the acquired images using the corrected data to obtain a position for each particle;
         characterizing each particle individually to obtain an intermediate analysis result which comprises the position and characterization parameters for each particle;
         classifying the particles based on the characterization parameters of each particle to obtain classification groups of particles (or particle classes);
         counting a number of particles per classification group for each acquired image;
         calculating an overall analysis result which comprises at least one statistical value, which is calculated, for each biomarker in each sample of the biosensor, by using the number of particles per classification group for all the images acquired from the same sample, and the statistical value calculated per sample being correlated with an indication of the presence of a biomarker in the sample.

The present invention has a number of advantages with respect to prior art, which can be summarized as follows:

The present invention allows an ultra-fast spectral analysis of plasmonic nanoparticles with a throughput that is at least 100 times higher compared with the state-of-the-art in dark-field micro-spectrophotometry. As the proposed method obtains the spatial resolution and the spectral resolution of images simultaneously, a much faster measurement and a higher sample throughput are reached.

The counting of nano-particles is a "digital" technique: Instead of integrating the optical signal from labelled biomarkers over a certain area of the biosensor, the actual number of detected labelled biomarkers is counted. This makes the method much more robust and independent from the image acquisition parameters, e.g., the brightness or the spectrum of the illumination, and from variations of the biosensor substrate, of the nano-particles etc.

These and other advantages will be apparent in the light of the detailed description of the invention.

DESCRIPTION OF THE DRAWINGS

For the purpose of aiding the understanding of the characteristics of the invention, according to a preferred practical embodiment thereof and in order to complement this description, the following figures are attached as an integral part thereof, having an illustrative and non-limiting character.

PREFERRED EMBODIMENT OF THE INVENTION

The matters defined in this detailed description are provided to assist in a comprehensive understanding of the invention. Accordingly, those of ordinary skill in the art will recognize that variation changes and modifications of the embodiments described herein can be made without departing from the scope and spirit of the invention. Also, description of well-known functions and elements are omitted for clarity and conciseness.

Of course, the embodiments of the invention can be implemented in a variety of architectural platforms, operating and server systems, devices, systems, or applications. Any particular architectural layout or implementation presented herein is provided for purposes of illustration and comprehension only and is not intended to limit aspects of the invention.

A preferred embodiment of the invention refers to a method for determining the presence and/or the concentration of one or more biomarkers attached to a biosensor, in which the biomarkers are labelled with one or more types of nano-particles. The method includes data acquisition to obtain spatially and spectrally resolved information of the biosensor. This information is referred to as "images" in the following. The method analyzes this information ("images") to detect the presence of biomarkers, and to quantify their number and/or their concentration.

Figure 1:
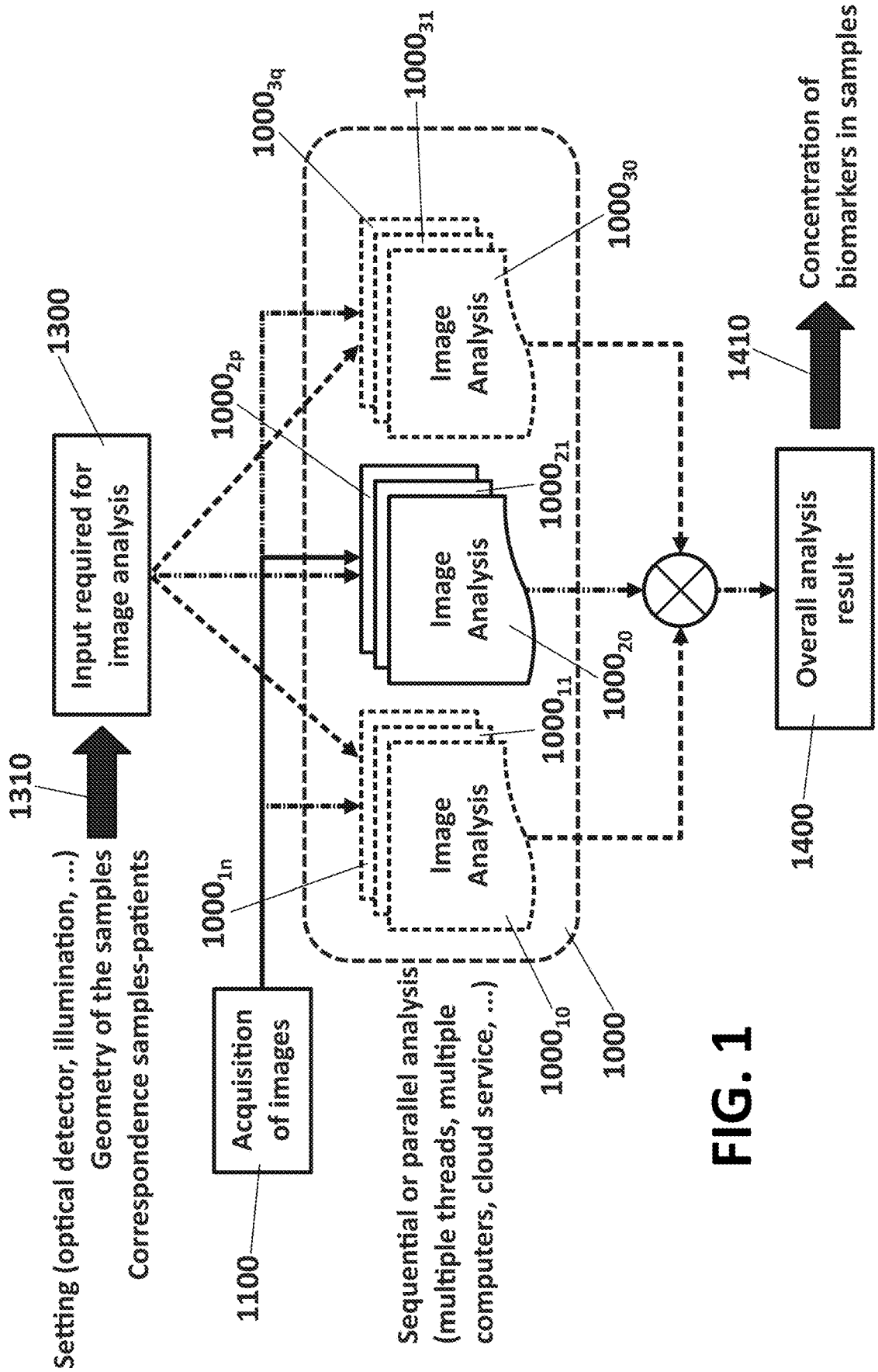
FIG. 1 shows a flowchart of a method for optically detecting biomarkers, according to a preferred embodiment of the invention.

FIG. 1 shows an overall workflow of the proposed method running the image analysis (1000) in parallel to the image acquisition (1100). The method can perform a sequential or a parallel image analysis (1000) by using multiple threads, multiple computers, cloud service, etc.

Typically, several images are analyzed in parallel ($1000_{10}$, $1000_{11}$, . . . $1000_{1n}$, $1000_{20}$, $1000_{21}$, . . . $1000_{2p}$, $1000_{30}$, $1000_{31}$, . . . $1000_{3q}$) as shown in FIG. 1. The input data (1300) required for the analysis (1000) comprises, in addition to the images, calibration parameters (1310) to adjust the measurement (e.g., the type of the camera used to capture the images, the type of light source used to illuminate the sample, geometry of the samples, correspondence of the samples with the patient, etc.). Once all images have been analyzed, an overall result is generated (1400), from which the concentration of biomarkers (1410) in the samples can be obtained.

Prior to the actual image analysis (1000), the acquisition parameters (1310) used for the acquisition of the input data (1100) by optical scanning and required for the image analysis (1000) are obtained (1300): typically, these parameters (1310) are read from a file or database, or entered manually by the user. These parameters (1310) comprise the number and locations of the samples and of the individual images on the biosensor, the type(s) of biomarker(s) present in the samples, the type(s) of nano-particles and biosensor substrate used, information on the sample volumes, the illumination, and the camera and image capture settings, etc. In a possible implementation, this information is automatically saved in one or more text files during an optical scanning, e.g., with one file containing information about the settings of camera, illumination, and auto-focus, and the second one containing information on the geometry of the samples on the biosensor, the geometry of the images within the area of each sample, and on the samples which have actually been scanned (i.e., all samples or a subset of them). In addition, the correspondence between the samples on the biosensor and patient information (e.g., which well/sample on the biosensor corresponds to which patient identifier) must have been stored; this information is not relevant for the analysis itself, but of course indispensable for the diagnostic use of its results. In a clinical environment, this information is typically stored in a central HIS (Hospital Information System). In a possible implementation, the information is edited by the person who prepares the biosensor and is stored in a folder on a network drive from which it can be read by both the optical scanner and the analysis software.

To acquire the input data or images (1100), a camera (e.g., an RGB camera) can be used to capture the images. An alternative to the use of a color camera could be i) an array of photodetectors coupled with an array of optical filters arranged in a mosaic pattern, ii) multiple arrays of photodetectors coupled with dichroic optical filters or iii) a vertically stacked array of photodetectors able to detect different spectral bands at the same spatial position. This kind of optical detectors is a viable technological solution for the simultaneous spatial and spectral analysis of a sample with sub-micrometrical resolution and at multiple spectral bands (typically at least 2 and not more than 30). The setting of parameters (1310) used for this image acquisition (1100) comprises adjusting the parameters of the camera to produce well-exposed images, regarding black and white level, white-balance, and color reproduction. The settings are chosen such that the nano-particles serving as biomarker labels can be well imaged, with signals above the noise level and below the saturation region (by adjusting sensitivity and exposure time) and resulting in a good discrimination between different particles in terms of the scattering spectrum ("color"; by adjusting the color-correction matrix).

In order to capture the images, an optical scanner is used. Typically, the biosensor to be scanned comprises different areas corresponding to different samples, very similar to a multi-well plate, with one well per patient sample.

The optical scanner proposed here is configured to acquire (1100) spatially and spectrally resolved images from a biosensor by the following steps:
 illuminating the biosensor at a glazing angle with a broadband continuous spectrum;
 focusing the surface of the biosensor onto an optical sensor using an auto-focus system;
 capturing spatially and spectrally resolved optical signals from the sample, by using an optical detector which simultaneously captures the scattered light coming from the sample with spatial and spectral resolution;
 moving in two spatial coordinates the biosensor and/or the optical head of the scanner with a motorization system to produce a relative movement between the sample and the optical scanner.

The spatial resolution on the biosensor is achieved with two means: the optical detector (i.e., the camera sensor), which itself provides spatial resolution, and the relative movement between the sample and the optical scanner. In a possible implementation, the biosensor is moved relative to the stationary optical head, by means of a two-axis motorized stage. Typically, more than one image is taken of each area corresponding to the same sample; still, the images taken typically do not cover the sample area completely. In a typical scan, the number of images taken per sample and their positions within the sample area can be the same for all sample areas of the biosensor. Still, this is not necessarily the best option; the numbers and positions can also be chosen individually for each sample, e.g., such to take more images for samples which have low concentrations of biomarkers, to improve the statistical robustness of the measurement. The overall number of images taken during a scan of the biosensor can range from one to many thousands.

The sub-division of the data acquisition in individual images has the important advantage that the analysis of those images can be performed in parallel to the scan, i.e., while keeping on acquiring images, which leads to a higher sample throughput.

Parallelization of the image analysis (1000): All (or a subset of all) the acquired images are analyzed. On a computer, this analysis can be performed strictly sequentially (one image per time) or analyzing several images in parallel (using multiple threads of the computer, e.g., one image per thread). Typically, a number of parallel threads close to the maximum available on the computer is chosen (=number of kernels or number of logical processors) to reduce the total time of the analysis. The parallelization can be with respect to the images (one image per thread) or subdividing each image and analyzing the sub-images in parallel.

In a possible implementation, the image analysis (1000) runs on the same computer which controls the data acquisition by the proposed scanner. The possibility that the information of interest on the biosensor can be obtained by analyzing different images independently is a great advantage of the technique: this way, the most time-consuming task (the analysis of each image) can be easily parallelized, and this parallelization can be scaled-up in a straightforward, efficient, and economically feasible way (computer with more kernels, several CPUs, several computers in a network etc.).

In another possible implementation, the images can be stored within a network and the image analysis (1000) can be run on a computer different from the one which controls the proposed scanner. Likewise, the analysis of all images can be split between several computers in the network, such that each computer analyzes a subset of the images. Both the storage and the analysis could be done using a cloud service. The images captured during the scan can be saved in a common image format, e.g., TIFF or JPEG, typically as RGB images with 8 bits per color channel. In most cases, JPEG is preferred, because the resulting files are smaller and can be both written and read more rapidly. On the other hand, JPEG uses a lossy compression which especially affects the color representation. Since the spectral characterization of the particles on the biosensor is an essential aspect of this invention, only a rather mild JPEG compression is used (i.e., a high "quality factor"), to minimize potential distortions in the color representation. In another embodiment, images can be saved with a larger color depth, e.g., as 16 bit-TIFF images, to avoid artefacts in the images in case of particles with low scattering intensities. In another possible embodiment, images can be saved as camera raw data, which preserves the full dynamic range of the camera sensor (typically 12-14 bits), and the linear dependence between the amount of scattered light and the signal measured by the sensor. In case of a sensor with multiple (more than three) spectral bands, typically the proprietary image format of the manufacturer must be used; apart from a RAW format, this can also be based on TIFF as container.

In order to reduce the time and the amount of memory required to store images, and the time to analyze them, the captured images are binned. Typically, a binning of 2×2 is applied, i.e., four sensor pixels result in one image pixel. Quadratic interpolation between pixels is used to calculate the binned images. Compared to the alternative of directly using a sensor with fewer pixels without subsequent binning of the images, this approach achieves a better discrimination between particles in terms of color. Thus, in a possible implementation, image binning is applied when using a camera with 12 MP; images from 4 MP cameras are not binned, because the remaining spatial resolution would be too low. Typically, the images are first stored locally on a hard disk of the computer which is part of the optical scanner. Alternatively, the images can be directly transferred to a different computer or storage system, within the network of the scanner's computer.

Storing the images to a storage device (e.g., to a hard disk) can be omitted if, instead, the image analysis (1000) of each captured image is performed directly with the image still being in the computer's memory or RAM.

The image analysis (1000) can be performed after the whole biosensor has been scanned, or it can run in parallel to the scan (e.g., every time that all images of a certain sample have been taken), so that the results are obtained as quickly as possible after the scan.

The image analysis (1000) can be implemented partly or totally in hardware, e.g., using FPGAs (field-programmable gate arrays) directly connected to the optical detector in order to reduce the required analysis time.

Figure 2:
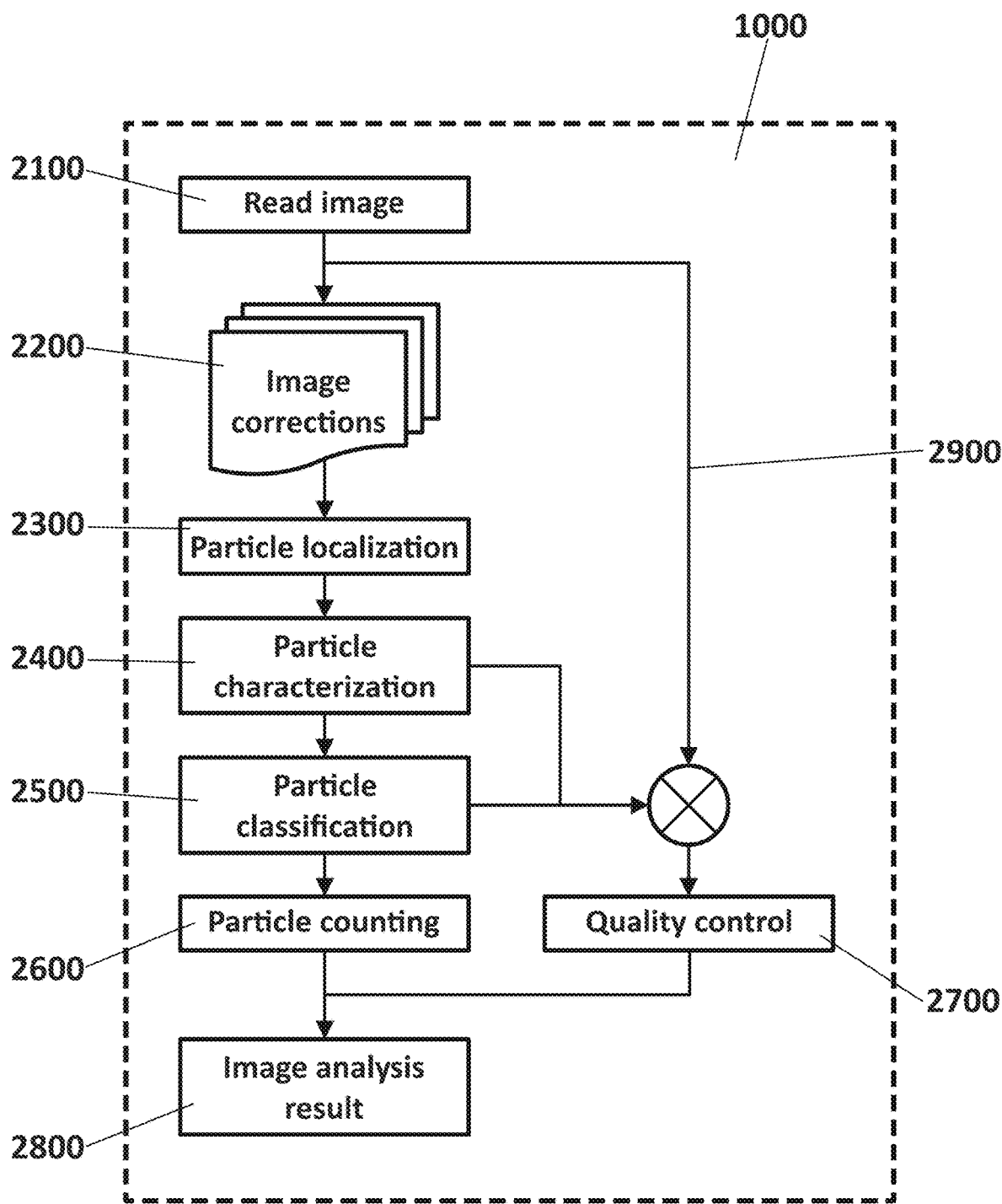
FIG. 2 shows a flowchart of the image analysis, according to a possible embodiment of the invention.

FIG. 2 shows a flowchart of the image analysis (1000) which illustrates the following steps performed for each image:

Reading (2100) the image: The image data is read from storage means (e.g., memory) described before.

Image corrections (2200): image corrections and/or transformations are calculated, if the corresponding option has been chosen by the user, or is activated by default, or is activated automatically based on the information on the scan (type of camera sensor used, imaging parameters etc.).

Particle localization (2300): Potential particles are localized in the image.

Particle characterization (2400): Each particle is characterized individually to allow the classification of the particles in the following step of the analysis.

Particle classification (2500): The particles are classified, which allows to consider only the particles that are most specific to the biomarker, being a step that is indispensable for multiplexing.

Particle counting (2600): Instead of integrating the optical signal from the labelled biomarkers over a certain area of the biosensor, the actual number of detected labelled biomarkers is counted, which makes the method much more robust and independent from the image acquisition parameters, e.g., the brightness or the spectrum of the illumination, and from variations of the biosensor substrate, of the nano-particles etc.

Quality control (2700): To evaluate the quality of the measurement in general and of each image in particular, quality indicators are deduced; these indicators being then used to guide the calculation of the analysis results at the next (final) step.

Overall analysis result (2800): In case that more than one image has been acquired for the same sample, a suitable statistical value is calculated from all images of the same sample (e.g., mean or sum of the values from the images, trimmed mean, median, quantiles etc.). The overall result for each sample and each biomarker can be qualitative (presence or absence of the biomarker) or quantitative (concentration of the biomarker). For example, the concentration (e.g., the amount of antigen in a certain sample volume) can be calculated from the number of nanoparticles.

FIGS. 3-7 show in further detail the flowcharts of the steps for image correction (2200) and particle localization (2300), characterization (2400) and classification (2500), which are described below.

Figure 3:
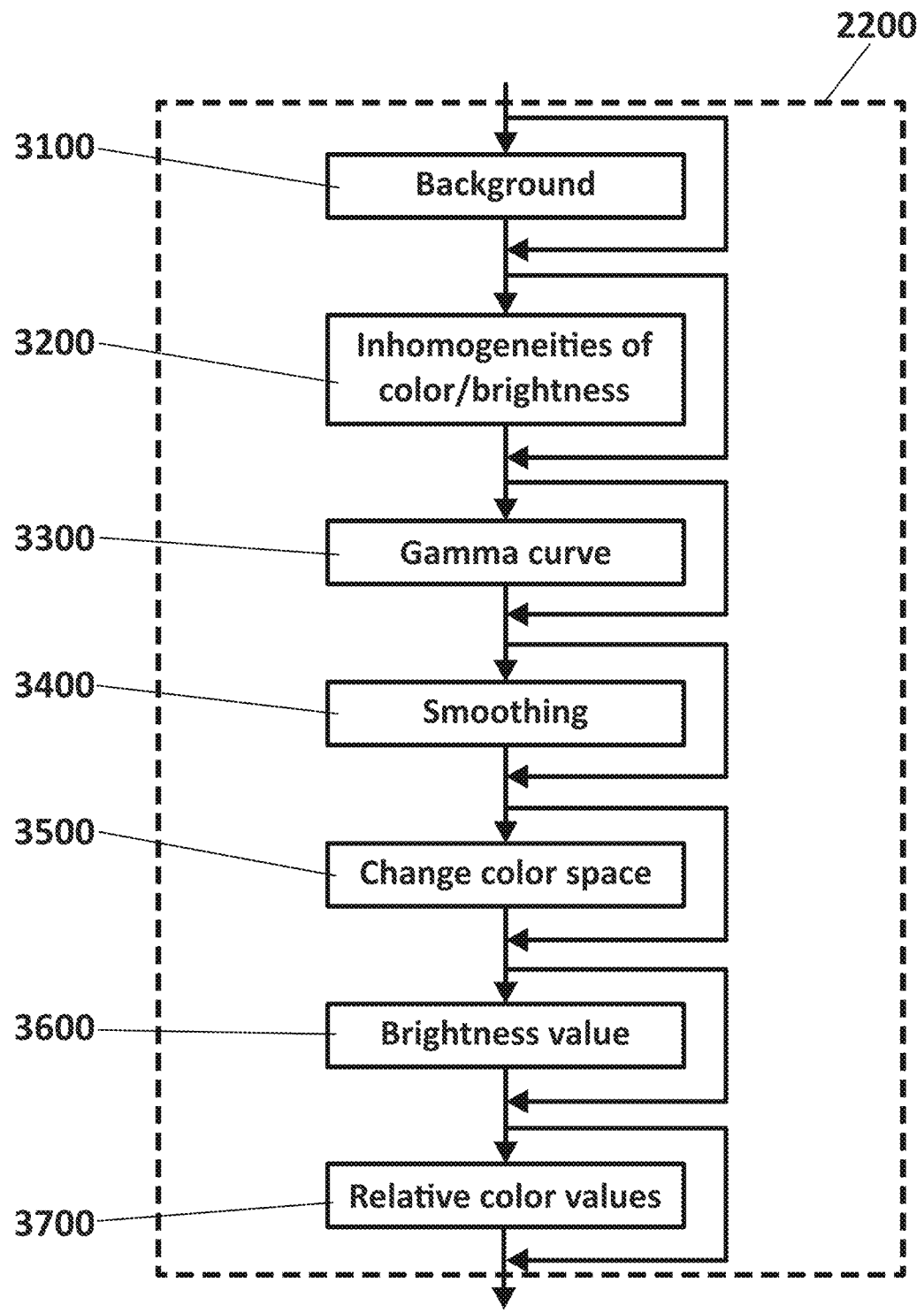
FIG. 3 shows a flowchart of the possible corrections and transformations of the image for the image analysis.

Image Correction (2200):

FIG. 3 shows the possible steps comprised by the step (2200) of image corrections and transformations for the image analysis (1000), in accordance with a preferred embodiment:

a) A background correction (3100) of the image is performed to adjust the black level. In a typical image from the optical scanner, the particles of interest appear as individual small bright spots on a dark background. Depending on the substrate, on the type of camera sensor, and on the acquisition parameters, this background might not appear "black" (i.e., sensor values close to zero, the "ideal" case), but "gray" (with or without a certain tint). An evaluation of the sensor values (e.g., based on a histogram of all pixels) allows the correction of both the signal offset and a potential tint. This simplifies the particles characterization (2400) in a later step of the image analysis (1000).

b) The image is corrected for potential inhomogeneities (3200) of the brightness and/or the color. Such inhomogeneities can be due to the illumination, the light collection, the camera sensor etc. A typical effect is that the center of the image appears brighter than the borders. A correction of these effects may be necessary to ensure a correct characterization (2400) and classification (2500) of the particles in the later steps of the image analysis (1000).

c) A modification of the gamma curve (3300) of the image is performed to adjust the dynamical range. "Gamma curve" refers to the dependence of the pixel values in an image on the actual (physical) quantity of detected light. In standard images (JPEG, TIFF etc.), this dependence is nonlinear in such a way that with increasing light, the pixel values increase slower than proportionally. In the proposed image analysis (1000), this nonlinear dependence is corrected, using the inverse function of the "gamma curve", so that the obtained pixel values are again proportional to the amount of scattered light.

d) The image data is smoothed (3400) to reduce image noise. As the actual optical resolution is typically larger than the pixel pitch on the camera sensor, the image noise (from the camera sensor, due to low light intensities etc.) can be reduced by smoothing (3400) without affecting the resolution. The reduction of image noise improves again the correct particle characterization (2400) and classification (2500).

e) In case of a standard color camera, a change/transformation to a different color space (3500) can be performed, e.g., from RGB to HSV, L*a*b etc., which can simplify the interpretation of the results from the particle characterization (2400) and result in a more precise discrimination of particles in terms of color. The L*a*b color space, e.g., contains one channel for the light intensity, L, while the other two axes describe the color; in comparison, the channels of RGB all mix color and brightness.

f) If the color space used does not contain a dedicated brightness value (e.g., in RGB), the brightness value (3600) is calculated by summing the color channels for each image pixel. The resulting gray-scale image is referred to as "brightness image" in the following. This brightness image is typically normalized, with "0" and "1" corresponding to the lowest and highest brightness level in the given image format (8 bit-RGB: (0|0|0)→0, (255|255|255)→1).

g) If the color space used does not contain relative color values, the relative color values (3700) can be calculated, for each pixel, by dividing each color channel by the sum of the channels, e.g., $R_{rel}=R/(R+G+B)$ for the relative contribution of the channel "Red".

In case that a camera with multiple spectral bands is used, the scattering intensities measured in each of the wavelength ranges of the sensor are used instead of the RGB values. Thus, the three values of a RGB image are simply exchanged for an array of elements representing the different wavelength regions. The number of elements is typically larger than three to gain spectral resolution. Still, also a combination of just two well-selected wavelengths can be a suitable choice for a precise discrimination between different particles.

Particle Localization (2300)

Figure 4:
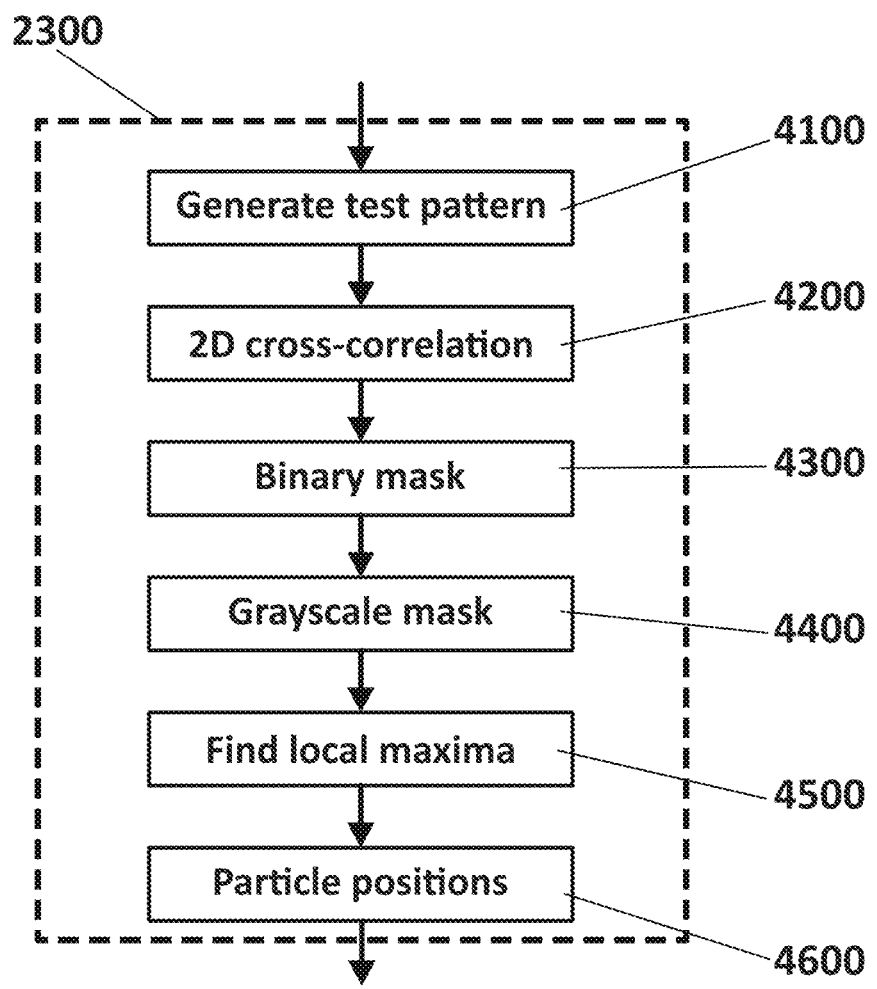
FIG. 4 shows a flowchart of the particle localization for the image analysis.

FIG. 4 shows the possible steps for the localization (2300) of particles, in accordance with a preferred embodiment:

a) A test pattern (4100) is generated which represents the typical shape of a nano-particle in an image from the optical platform, considering the actual image acquisition parameters used (optical and sensor resolution, magnification etc.). Preferably, a single gray-scale test pattern is used. The shape of a nano-particle can be represented, e.g., by a two-dimensional Gaussian function, by an Airy pattern, a simple disc shape, etc. In a possible implementation, a sum of two Gaussian functions ($G_1+(-G_2)$) is used to approximately match the typical "donut" shaped scattering pattern of individual plasmonic nano-particles.

Instead of a single gray-scale test pattern, a pattern with colors can be used, e.g., with one pattern for each RGB component, or for each channel of a camera with multiple spectral bands. This can improve the correct identification of potential particles in the case that the shape depends on the wavelength (e.g., Gaussian shaped in the green and donut shaped in the orange spectral range).

b) The normalized two-dimensional cross-correlation (4200) between the brightness image and the test pattern (or patterns) is calculated. This cross-correlation image (4200) has values close to "1" for regions of the image that are similar in shape to the test pattern.

Instead of using the brightness image, the cross-correlation (4200) can be calculated between the test pattern and, e.g., one of the color channels of the image (or a linear combination of several channels, or some other function). This is a suitable approach if, e.g., a certain pattern is more pronounced in one channel compared to the others.

c) A mask (4300) is calculated for the image. For example, a binary mask is defined, wherein the mask equals "1" (=true) for pixels with a cross-correlation value above some threshold (e.g., >0.6) and a relative brightness in a certain range (e.g., >0.03 and <0.98, i.e., above noise and below saturation). All other pixels are zero (=false).

Instead of a binary mask ("0" or "1"), continuous values can be used to define the mask (4300), i.e., a gray-scale mask with values (e.g.) close to one if the constraints are well matched, and close to zero if not, with all values in between possible.

The given threshold values for correlation and brightness are just examples; based on the actual measurements better suited values can be selected, or thresholds on different and/or additional parameters can be chosen (color, signal-background ratio etc.).

d) A grayscale mask (4400) is generated by multiplying the previous defined mask (4300) pixelwise with the cross-correlation image (4200). Instead of using the product of the binary mask with the cross-correlation image, the positions of the potential particles can be derived from the binary mask only (location of the regions with value "1"). Instead of the product, other functions have been used, e.g., taking the square of the cross-correlation image, etc.

e) From the resulting grayscale image (4400), the local maxima, i.e., pixels with values higher than those of all their direct neighbors, are localized and the positions of these local maxima are considered potential positions (4500) of particles. Instead of using the cross-correlation (4200) with a test pattern (4100) at all, the particle search can also be based on thresholding techniques (e.g., everything above a certain background value is considered a potential particle), on the Hough transformation of the image (e.g., find circular objects of a certain size), etc.

Particle Characterization (2400)

Figure 5:
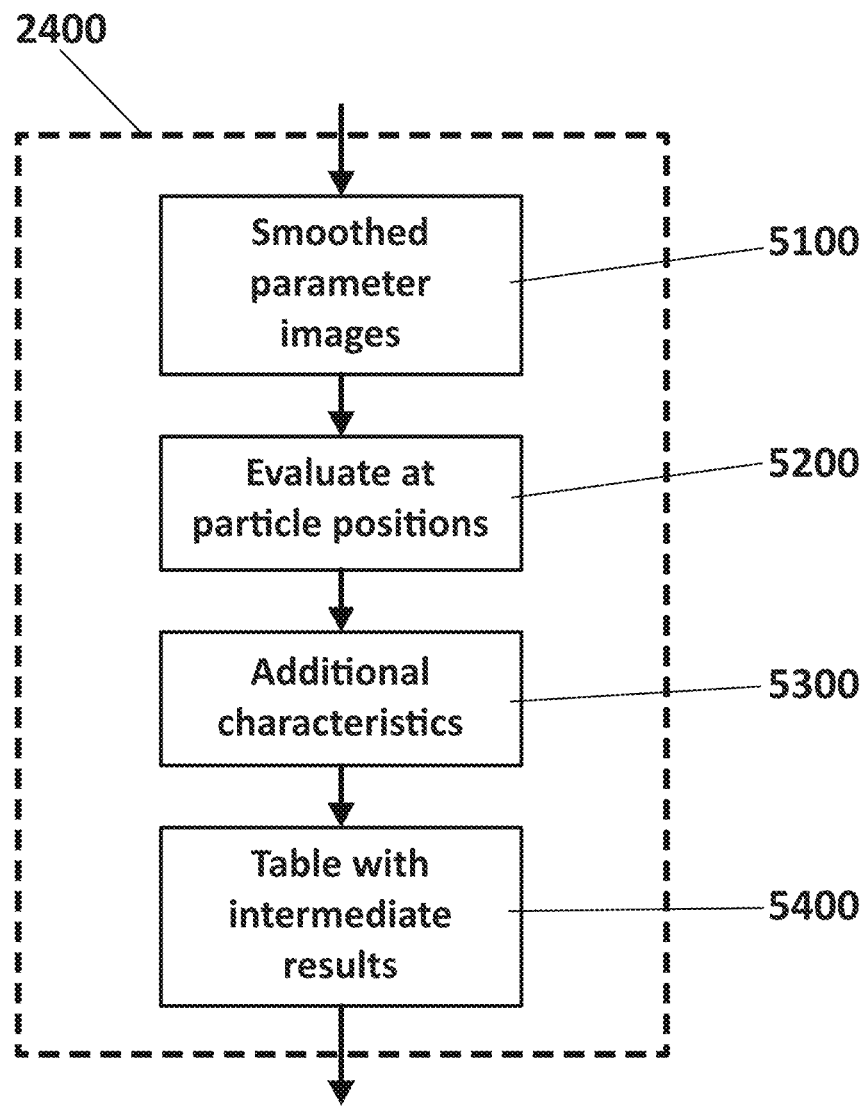
FIG. 5 shows a flowchart of the particle characterization for the image analysis.

FIG. 5 shows the possible steps for the characterization (2400) of particles, in accordance with a preferred embodiment:

a) Obtain smoothed parameters (5100) of the images: The parameters of highest interest are the brightness and the scattering spectrum ("color") of each particle. To obtain average values of these parameters (i.e., averaged over the area of the particle), the corresponding images (brightness image, image with relative color contributions etc.) are filtered with a suitable kernel, e.g., a two-dimensional Gaussian with a size close to the expected particle size, or with a disc-shaped pattern.

b) These filtered/smoothed images are evaluated (5200) at the potential particle positions (4500) calculated before. In case that the number of particles per image to be characterized is "low", it can be computationally inefficient to calculate the convolution of the whole image with a kernel to extract the mean values. Instead, it is a more efficient option to directly extract a small region from the image around each particle and use it to derive the mean values. What is considered a "low" number depends on the imaging parameters, the hardware of the computer, and the implementation of the analysis routines. For a given setup, the crossover point can be determined, such that one or the other option can be used automatically.

c) Additional characteristics (5300) of interest are the particle's size and shape, e.g., the FWHM—Full Wdth at Half Maximum—in the brightness image, the degree of correlation with the test pattern, and the local shape at the center of the particle. The latter parameter allows to distinguish a donut shape (=indention at the center) from a Gaussian (or similar) shape (=maximum at the center). The analysis used in the current implementation calculates a value that is proportional to the Discrete Laplacian at the center of the particle; this choice permits an efficient implementation based on a simple convolution of the image with a 3×3 kernel. Further additional characteristics (5300) of interest are the local particle density (e.g., based on nearest neighbor distances), and further spectral characteristics (e.g., differences or ratios of spectral components).

d) As a result, the characteristics of each potential particle are obtained and their positions are already known from the previous step of particle localization (2300). For each image, particle characteristics and positions define an intermediate result (5400) represented as a table, with one row for each potential particle, and as much columns as characteristics have been derived, see Table 1 below for an example.

TABLE 1

| x | y | I | R | G | B | ... | ... |
|---|---|---|---|---|---|---|---|
| 12 | 36 | 0.13 | 0.45 | 0.33 | 0.22 | | |
| 17 | 20 | 0.57 | 0.42 | 0.34 | 0.23 | | |
| 18 | 102 | 0.02 | 0.33 | 0.37 | 0.30 | | |
| ... | | | | | | | |

Table 1 illustrates an example result from the characterization (2400) of one image, wherein each row of the table corresponds to one particle, x and y are its coordinates in the image, I denotes its brightness, and R, G, B are the relative color contributions respectively. Depending on the analysis, more columns can be added for additional characterization parameters.

Particle Classification (2500)

Figure 6:
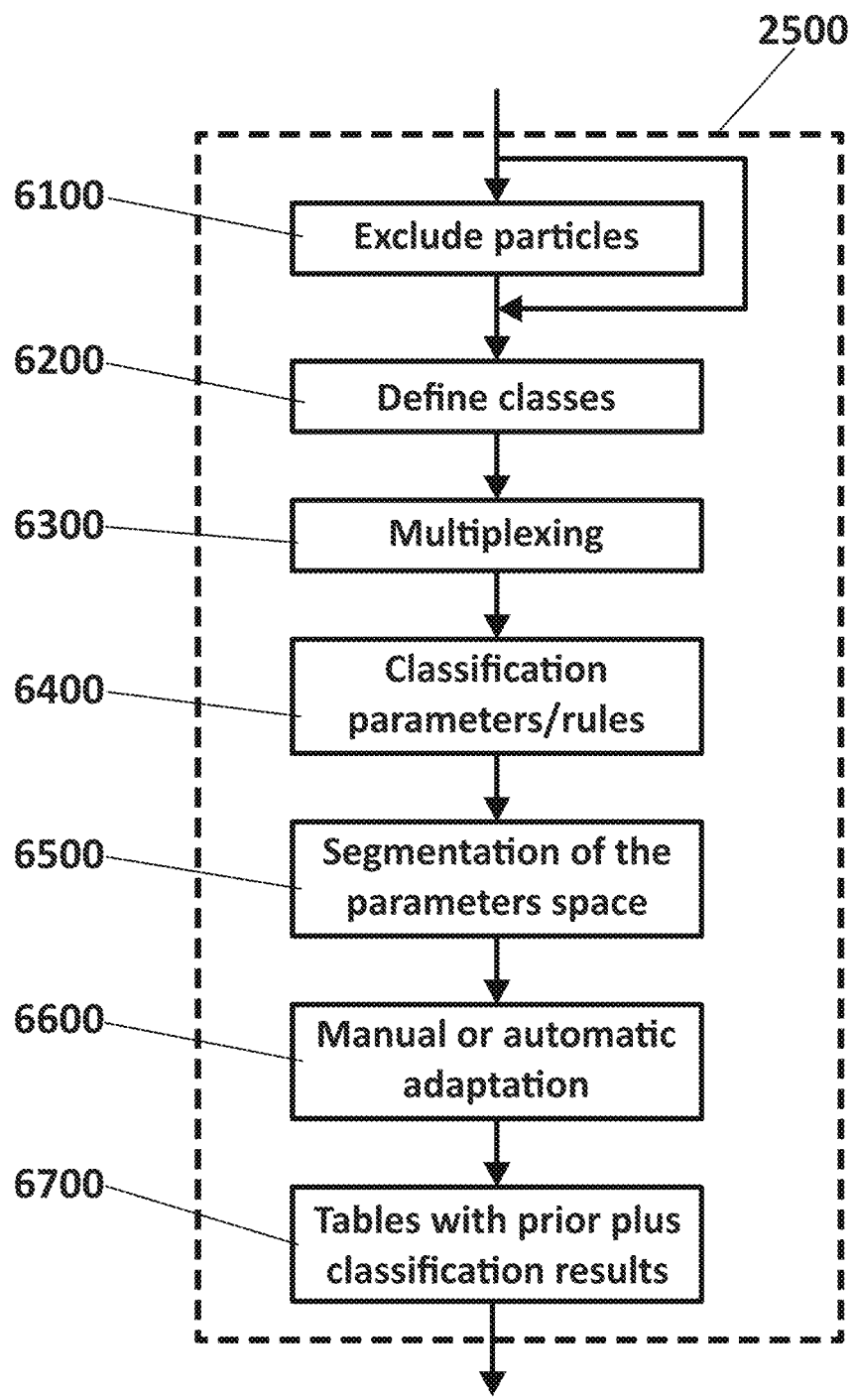
FIG. 6 shows a flowchart of the particle classification for the image analysis.
Figure 7:
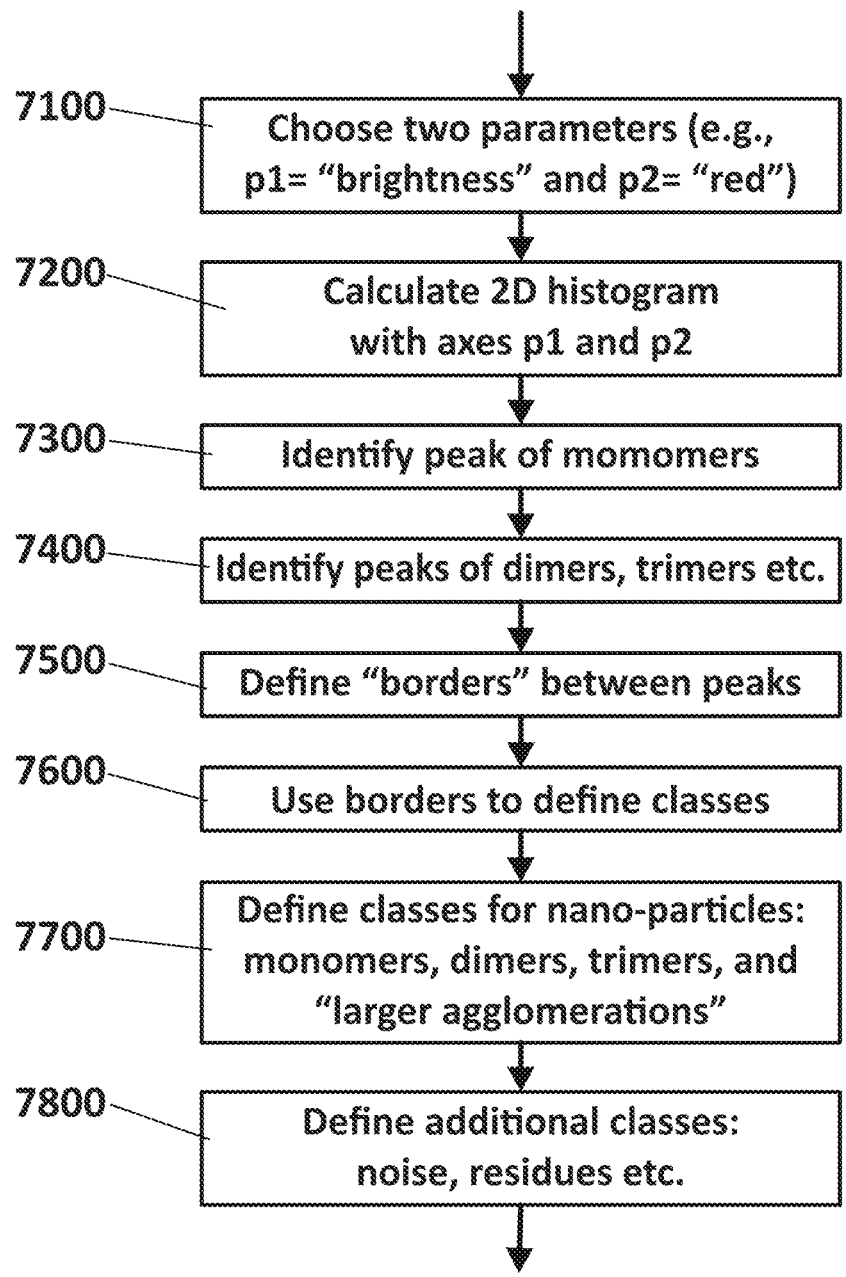
FIG. 7 shows a flowchart of the classification rules used for the particle classification.

FIG. 6 shows the possible steps for the classification (2500) of particles, in accordance with a preferred embodiment:

a) If required, certain characteristics can be used to exclude particles (6100) from the further steps of particle counting (2600), quality control (2700), and final result (2800) of the image analysis (1000). For example, if only monomers of nano-particles are of interest, and monomers show a donut shape as a distinguishing feature, this parameter can be used to eliminate all non-donut shaped particles.

b) Based on information of previous analysis, different classes (6200) of particles are defined based on their characteristics (brightness, "color", shape, size), e.g.,
  (1) noise (very low brightness),
  (2) residues from the biosensor fabrication (certain spectral pattern),
  (3) dust (different spectral pattern),
  (4) individual nano-particles (distinct spectral pattern, brightness, shape etc.),
  (5) clusters of nano-particles (dimers, trimers etc., based on spectral pattern, brightness). For these clusters, their brightness typically depends systematically on the brightness of the corresponding individual nano-particle. This information is used to improve the classification.

c) In case of multiplexing (6300), i.e., simultaneous detection of various biomarkers, each one labelled with a different nano-particle, additional classification groups are defined to account for all nano-particles used, as shown later in FIG. 10 for particle counting (2600).

d) The necessary classification parameters and rules (6400), defining which combinations of characteristics correspond to each class, can be given before-hand based on previous measurements or can be derived from the measurement to be analyzed itself as shown in FIG. 7. In the latter case, this analysis is typically based on the combined results from all images of a measurement, not on each one individually (to improve statistics, and to ensure that the classification is consistent among all images).

e) The classification consists basically in a segmentation (6500) of the parameter space. Its rules can be defined by the operator (e.g., manual segmentation), or can be derived automatically (e.g., cluster search, k-means method, segmentation algorithms, machine learning algorithms etc.). In case of an RGB camera, an example for a classification is that all particles with a normalized brightness in the range [>0.1, <0.7] and a relative contribution of the color channel "Red" in the range [>0.0, <0.33] are considered residues from the fabrication.

f) The classification can be manually or automatically adapted (6600) in case of differences between nano-particle lots, changes in the illumination, changes in detection parameters, etc.

Figure 8:
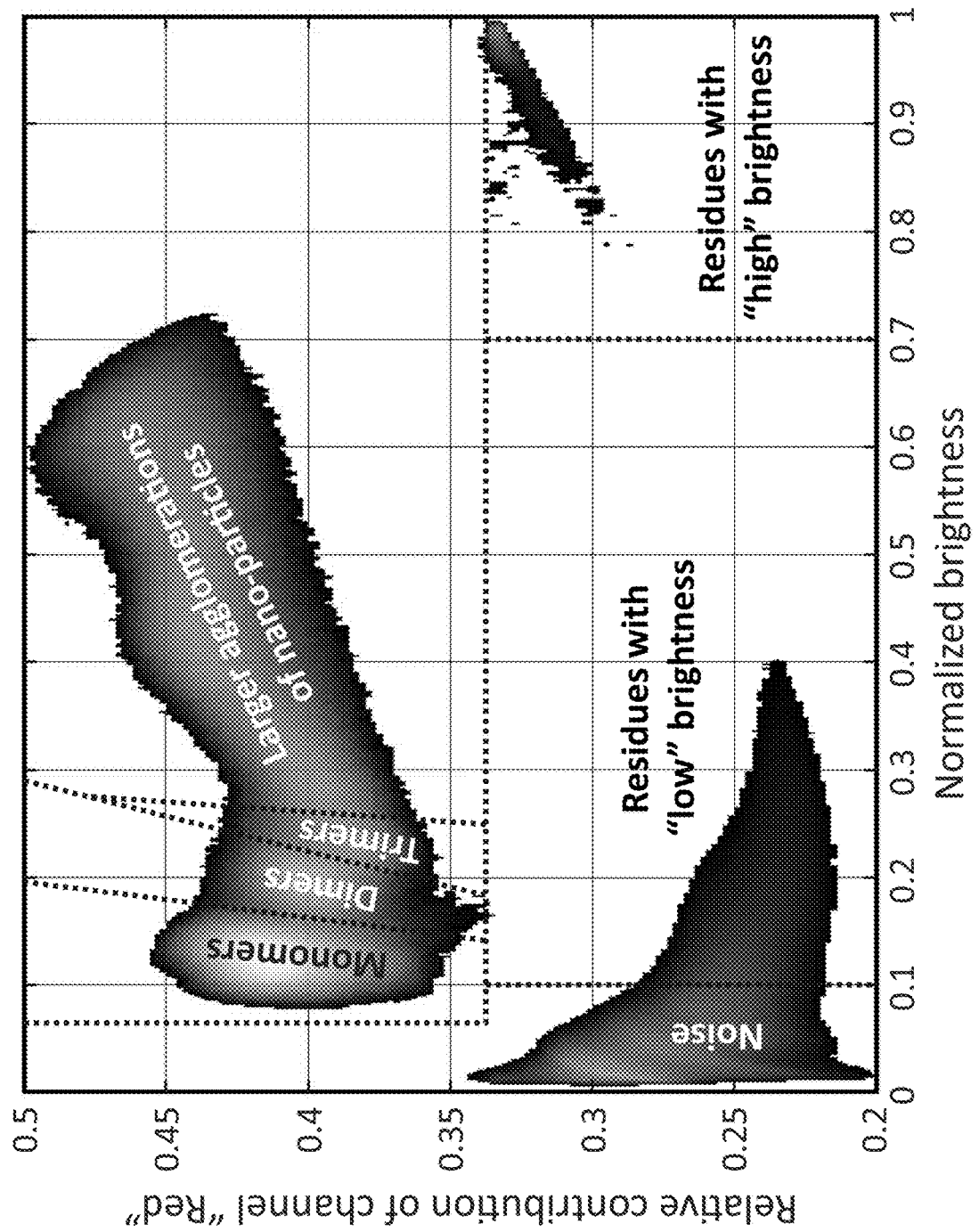
FIG. 8 shows a two-dimensional density distribution of characterization parameters for particle classification.
Figure 9:
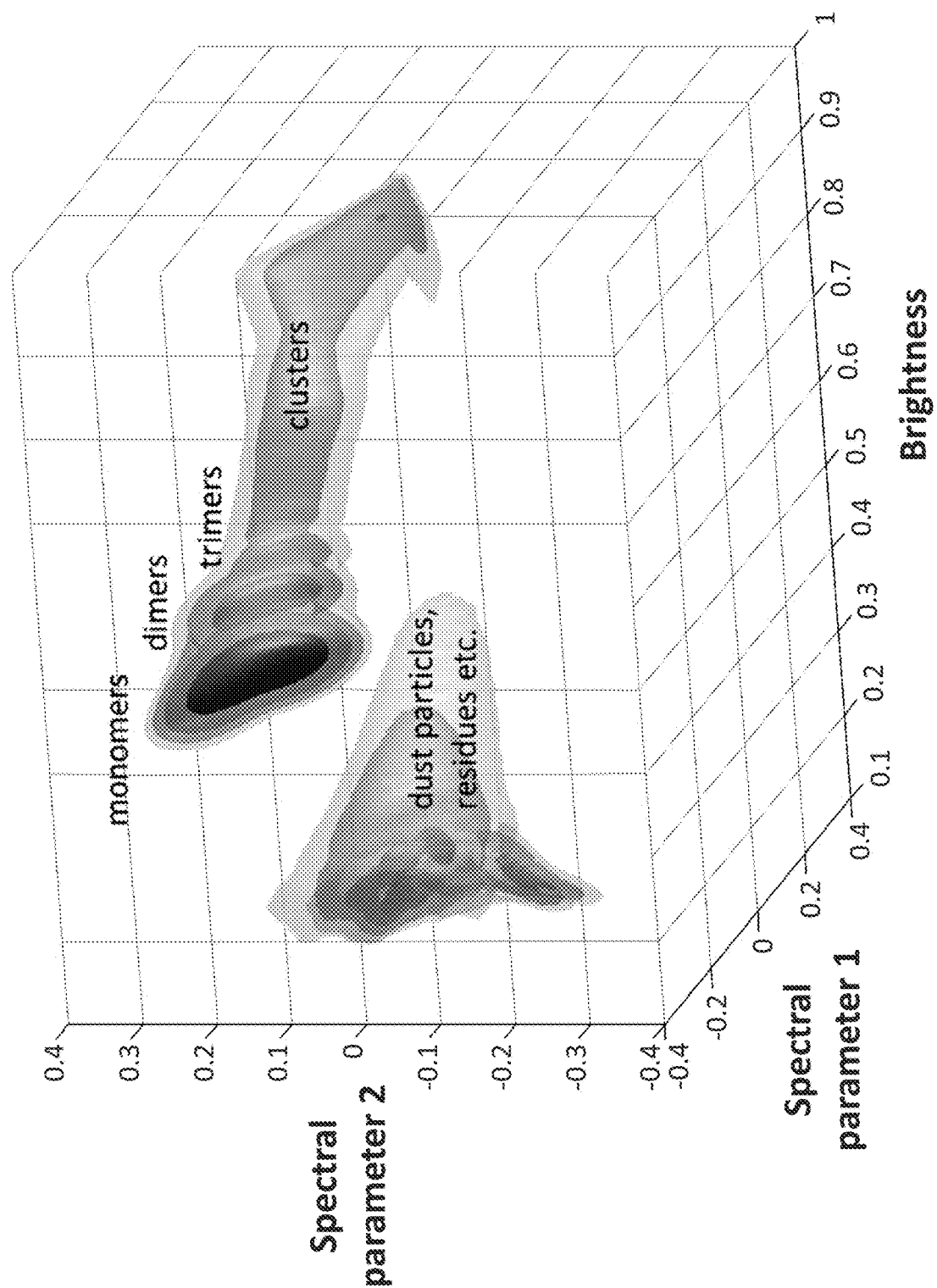
FIG. 9 shows a three-dimensional density distribution of characterization parameters for particle classification.

In a possible implementation, the classification rules can be derived as shown in 7 and explained below:

i. The characterization parameters (preferably, two parameters: brightness and color component) are chosen (7100) and a histogram (7200) of these parameters from all potential particles is calculated. In case of an RGB camera, typically the normalized brightness and the relative contribution of the channel "Red" are used as parameters. FIG. 8 illustrates a two-dimensional histogram of two parameter values: the normalized brightness of the particles being represented along the horizontal axis, and the relative contribution of the channel "Red" represented along the vertical axis. The monomers, dimers, trimers etc. of the nano-particles form "peaks" in this histogram and the lines drawn in FIG. 8 indicate the borders between the different types of particles. The use of two parameters and the calculation of the corresponding two-dimensional histogram is just an example. If more parameters are used, the mathematical steps are essentially the same. For example, in case of three parameters a three-dimensional density distribution ("histogram") could be obtained, as shown in FIG. 9, and instead of separating lines, separating planes (or other surfaces) are used between the different types/classes of particles.

ii. In the calculated histogram, the "peak" of the monomers is identified (7300). Particles of the same type (e.g., individual nano-particles) form a sort of "peak" (="dense" region of the histogram, or, in general, of the parameter space), because all of them have similar values of brightness and color. They are similar and not identical because of differences in the individual particles, and due to noise and/or lack of precision in the measurement. In a typical measurement, the main "peak" corresponds to individual nano-particles (monomers). Based on knowledge from previous measurements, the location of this "peak" in the histogram of the data to be analyzed can be identified automatically, searching the local maximum of the histogram in a given parameter range, e.g., normalized brightness in [0.1, 0.3] and relative contribution of channel "Red" in [0.35, 0.45].

iii. Once this location of the monomers is known, the positions of dimers, trimers etc. can be estimated (7400) based on the knowledge that their brightness is approximately two times, three times etc. that of the monomers. Again, the estimates are used to guide the search for the actual local maxima.

iv. The peaks of monomers, dimers etc. tend to overlap somewhat. To assign a particle to either one or the other peak, a "border" between the two peaks is defined (7500) to distinguish classes of particles. A routine searches for a (straight) line that best defines the "valley" in between the two peaks.

v. The locations and separating lines between monomers, dimers, trimers, and larger agglomerations of nano-particles in the histogram are identified as described above. The borders are then used (7600) to define different classes of particles, such as, e.g., a dimer would then be that the parameters of the particle correspond to a point in the histogram which is "to the right" (=higher normalized brightness) of the "border" separating monomers and dimers, and to the left (=lower brightness) of the "border" separating dimers and trimers. In addition, the data point must be in a certain range regarding the contribution of the channel "Red" (e.g., larger than 0.34 and smaller than 0.6). In a preferred implementation, the nano-particles are classified (7700) as monomers, dimers, trimers, and "larger agglomerations" (i.e., A/4). Apart from the automatically adapted four rules for monomers, dimers, trimers, and larger agglomerations of nano-particles, fixed rules are defined for additional classes (7800) of particles, e.g. four more types of "particles" can be defined as follows:

(1) Noise: All "particles" with a normalized brightness below 0.1, and not belonging to the already defined groups of nano-particles.

(2) Residues with low brightness: "Red" below 0.33, brightness in the range [>0.1, <0.7].

(3) Residues with high brightness: "Red" below 0.33, brightness in the range [>0.7, <1.0].

(4) Saturated particles: Containing image pixels with brightness values equal to one (=saturated).

g) As a result, a classification of all potential particles is obtained (6700). The representation of this result is based on the tables generated in the step of characterization (2400), adding a column with the classification result, as show in Table 2 below.

TABLE 2

| x | y | I | R | G | B | ... | ... | class |
|---|---|---|---|---|---|---|---|---|
| 12 | 36 | 0.13 | 0.45 | 0.33 | 0.22 | | | 4 |
| 17 | 20 | 0.57 | 0.42 | 0.34 | 0.23 | | | 7 |
| 18 | 102 | 0.02 | 0.33 | 0.37 | 0.30 | | | 1 |
| ... | | | | | | | | |

Table 2 illustrates the result obtained after the nanoparticle classification (2500), for one image. Compared to Table 1Table$_1$, one additional column has been added to the right, indicating the "class" to which the corresponding particle belongs. In the example, the classes are denoted using integer numbers.

Particle Counting (2600)

The counting (2600) of particles works as follows:

a) The number of particles in each classification group is counted.

b) This "counting" can be direct (one particle, one count) or weighted (e.g., with the brightness of each particle in a group, or with an estimate of the probability of a correct classification etc.).

c) As a result, the number of particles per classification group is obtained for each image. This result can be represented, e.g., as a table with one row per image, and one column for each classification group.

Figure 10:
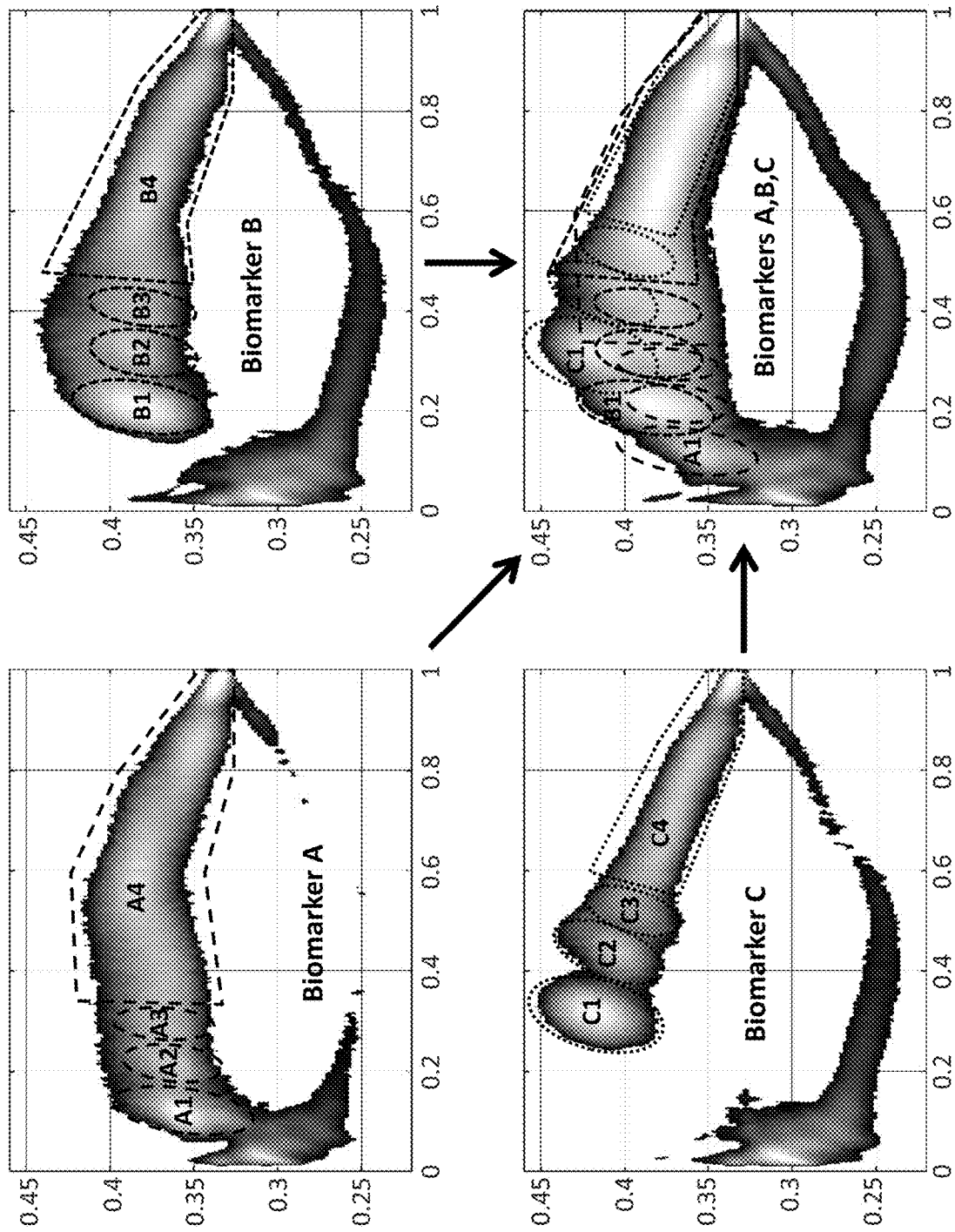
FIG. 10 shows a representation of the parameter space for the classification of particles in case of multiplexing.

In case of multiplexing, certain groups may overlap significantly in the parameter space, e.g., the clusters (dimers, trimers etc.) of a less-bright nano-particle with the monomers of a different (brighter) nano-particle, as shown in FIG. 10. In this case, the calculated number of particles must be corrected taking into account the following:

a) Measurements in which only one type of nano-particle is present are used to calculate the ratios between monomers, dimers, trimers etc. of each type of nano-particle used in the multiplex.

b) For these particles, it is calculated which fraction of them would fall into the regions of the parameter space which belong to the further types of nano-particles used.

c) Starting, e.g., with the monomers of lowest brightness, their number is used to estimate the numbers of corresponding dimers, trimers etc., and how many of them appear in the regions of the parameter space corresponding to the other nano-particles.

d) These numbers are used to correct the number of particles counted in a certain region, i.e., the number of clusters is subtracted from the uncorrected count.

e) The procedure is repeated for the rest of the nano-particles, e.g., in order of increasing brightness.

FIG. 10 illustrates the classification of particles in case of a multiplex, assuming three biomarkers: biomarker A, biomarker B, and biomarker C. Here, the same representation of the parameter space has been chosen as in FIG. 8, that is, one color component vs. brightness. Individually for each biomarker A, B, C, the monomers (A1, B1, C1), dimers (A2, B2, C2), trimers (A3, B3, C3), and larger agglomerations (A4, B4, C4) can be respectively identified. Comparing biomarkers A, B, and C, the position of the "mountains" in the histogram changes, because the three types of nano-particles used as labels have different brightness and scattering spectrum. In a multiplex, all the three biomarkers appear together, as shown in the lower right graphic of FIG. 10; the three monomers (A1, B1, C1) are well separated, but, e.g., the dimers of biomarker C (C2) overlap with the monomers of biomarker B (B1).

In case of substantial overlap between the "mountains" from two (or more) types of particles, the assignment of a simple border between them might result in a significant number of wrongly classified particles. This can be reduced with an alternative approach: A suitable sum of functions is used to fit the histogram or density distribution obtained from all images, with at least one component for each particle type ("mountain") of interest. Then, for all particles of each image (or all particles corresponding to the same sample), the weights of these components are determined which best match the histogram of this image (or sample), and these weights are used instead of the previously explained particle count.

Quality Control (2700)

To evaluate the quality of the measurement in general and of each image in particular, the area of the image in which saturation occurs is calculated (i.e., regions in which the normalized brightness is close to one), and a value representative of the degree of focus of the image is derived (e.g., the mean measured size of individual nano-particles).

Apart from a general quality control, these values can be used to guide the calculation of the overall analysis results (2800).

Overall Analysis Result (2800)

At least one statistical value is calculated from all images of the same sample. In a possible implementation, a trimmed mean with a symmetrical trimming of 40% can be calculated from all images of the same sample. In the calculation of this value, the parameters which correlate with the images quality (2700) can be used to guide the selection of the most representative images of a sample, e.g., omitting those images which have too large areas in which saturation occurred (e.g., saturated area>10%), or which are not well focused (e.g., FWHM of monomers>1 µm). For each sample, a value is calculated which correlates with the amount of biomarker present in the sample. In case of multiplexing, one such value is calculated for each biomarker. A suitable choice for this value is the number of individual nano-particles used as labels. The result can be presented as the mean number of particles per image, as a particle density (e.g., particles per mm$^2$), or as an extrapolation to the total number of particles within the sample area (an extrapolation because the images taken typically do not cover the whole area). The latter representation is preferred because it is the most direct to interpret, meaning that in a certain (known) quantity of patient sample used on the biosensor, this number of biomarkers has been detected.

The values presented to the user are provided with a suitable measure of their uncertainty, e.g., based on their standard deviation or their coefficient of variation (CV). These uncertainties can be estimated from the variations among the various images from the same sample, and/or from variations within the individual images. They can be directly reported as numbers (N±ΔN particles), and/or be used to indicate that a result is reliable or not.

If the uncertainty of the result for a sample is higher than a certain limit, the analysis software can feed back this finding and the scanner could take additional images of the corresponding sample, to verify if a consistent result can be obtained.

As a further step, the analysis results (2800) could directly guide the whole scan, i.e., for each sample, images are acquired until certain target values are fulfilled by the quality parameters, or an upper limit of the time or the number of images per sample is reached.

The described steps of the image analysis were performed in a proof-of-concept experiment, where a biosensor for the detection of two biomarkers was prepared: a biosensor with 96 wells was used and 8 different biomarker concentrations (from 1 fg/ml to 1 ng/ml, plus a negative control) were replicated 12 times each. The biosensor was scanned with the proposed optical scanner and the analysis was performed as described before. A Si-based multidielectric substrate of size 120 mm×80 mm was used for the biosensor. After silanization of the surface, a self-assembled monolayer based on a 1:1 mixture of the two capture antibodies for the biomarkers of interest was grown. Partitioning of the biosensor in 96 rectangular wells was achieved with a removable superstructure. Spherical gold nano-particles, GNPs, with diameters of 100 nm and 80 nm were functionalized with IL-6 and IL-10 detection antibodies, respectively. A 1:1 mixture of the two types of functionalized GNPs was prepared. For the samples, a buffer solution of phosphate-buffered saline (PBST) and fetal bovine serum FBS, PBST-25% FBS, was spiked with serially diluted biomarkers (1:10), resulting in final concentrations from 1 ng/ml to 1 fg/ml, plus a negative control; 200 μl of solution was used per well. The distribution of the samples on the 96-well biosensor is shown in Table 3 below: concentration of each biomarker is indicated in 1/ml and value "0" is the negative control, each concentration (rows 1 . . . 8) is replicated twelve times (columns 1 . . . 12).

TABLE 3

|   | 1 | 2 | ... | ... | 11 | 12 |
|---|---|---|---|---|---|---|
| 1 | 0 | 0 | | | 0 | 0 |
| 2 | 1 fg | 1 fg | | | 1 fg | 1 fg |
| 3 | 10 fg | 10 fg | | | 10 fg | 10 fg |
| 4 | 100 fg | 100 fg | | | 100 fg | 100 fg |
| 5 | 1 pg | 1 pg | | | 1 pg | 1 pg |
| 6 | 10 pg | 10 pg | | | 10 pg | 10 pg |
| 7 | 100 pg | 100 pg | | | 100 pg | 100 pg |
| 8 | 1 ng | 1 ng | | | 1 ng | 1 ng |

After the two incubation steps, first with the samples, then with the GNPs, the 96-well superstructure was removed. The biosensor substrate was washed several times, and finally blown dry with dry nitrogen.

Reading the Images

In this experiment, the optical scanner or reader was built with the following components:
dark-field microscope objective 50×/0.8
dark-field EPI illumination using a high-power white-light LED source
camera with 12-megapixel CMOS RGB sensor
2×2 binning of images applied before storage in JPEG file format.

Within each well of the biosensor 13×13 images were taken. The acquisition time for the total of 16224 images was about 100 min, i.e., almost 10,000 images/hour. The high number of images was chosen to permit a detailed analysis of the homogeneity of the biosensor. For the principal result of interest, the concentrations of the two biomarkers, a much smaller number of images would have been sufficient; acquisition of, e.g., 3×3 images would have required only about 5:20 min. The magnification of the microscope objective and the size of the camera sensor result in images that correspond to a field of view of 208×284 pmt on the biosensor; with 1504×2056 pixels after binning, the image scale was 0.138 μm per pixel.

The analysis of the images was performed on the same computer that controlled the optical scanner, in parallel to the data acquisition. Each time all 169 images of one well had been acquired, they were analyzed in parallel using 11 threads running on the computer.

Image Corrections and Transformations

Since the RGB format of the images does not provide independent brightness and color values, such normalized values were calculated first:
brightness=sum of RGB values, normalized to range 0 . . . 1;
relative components=each RGB component divided by the sum of the RGB values, also normalized to range 0 . . . 1.

Particle Localization

The localization of the particles was performed as described previously. A gray-scale pattern consisting of the sum of two 2-dimensional Gaussian functions was used, to match the donut shape of the emission from individual gold nano-particles; the FWHM (full-width at half maximum) of the pattern corresponded to an apparent particle size of 0.7 μm. A correlation of at least 0.6 between pattern and image was used as acceptance criterion for a potential particle; a lower threshold of 0.03 relative brightness was set to localize even potential particles with less than 10% of the brightness of a GNP.

Particle Characterization

To obtain average values of the intensity and the emission spectrum of each particle, the previously calculated image layers (normalized brightness, normalized relative color components) were smoothed with a Gaussian filter with a sigma of 2.5 pixels, which corresponds to an averaging over an image area with a FWHM of roughly 0.8 μm, i.e., close to the typical apparent particle size. The filtered layers were evaluated at the positions obtained in the localization step, resulting in a list of characteristics for each particle (one list per image).

Particle Classification

Figure 11:
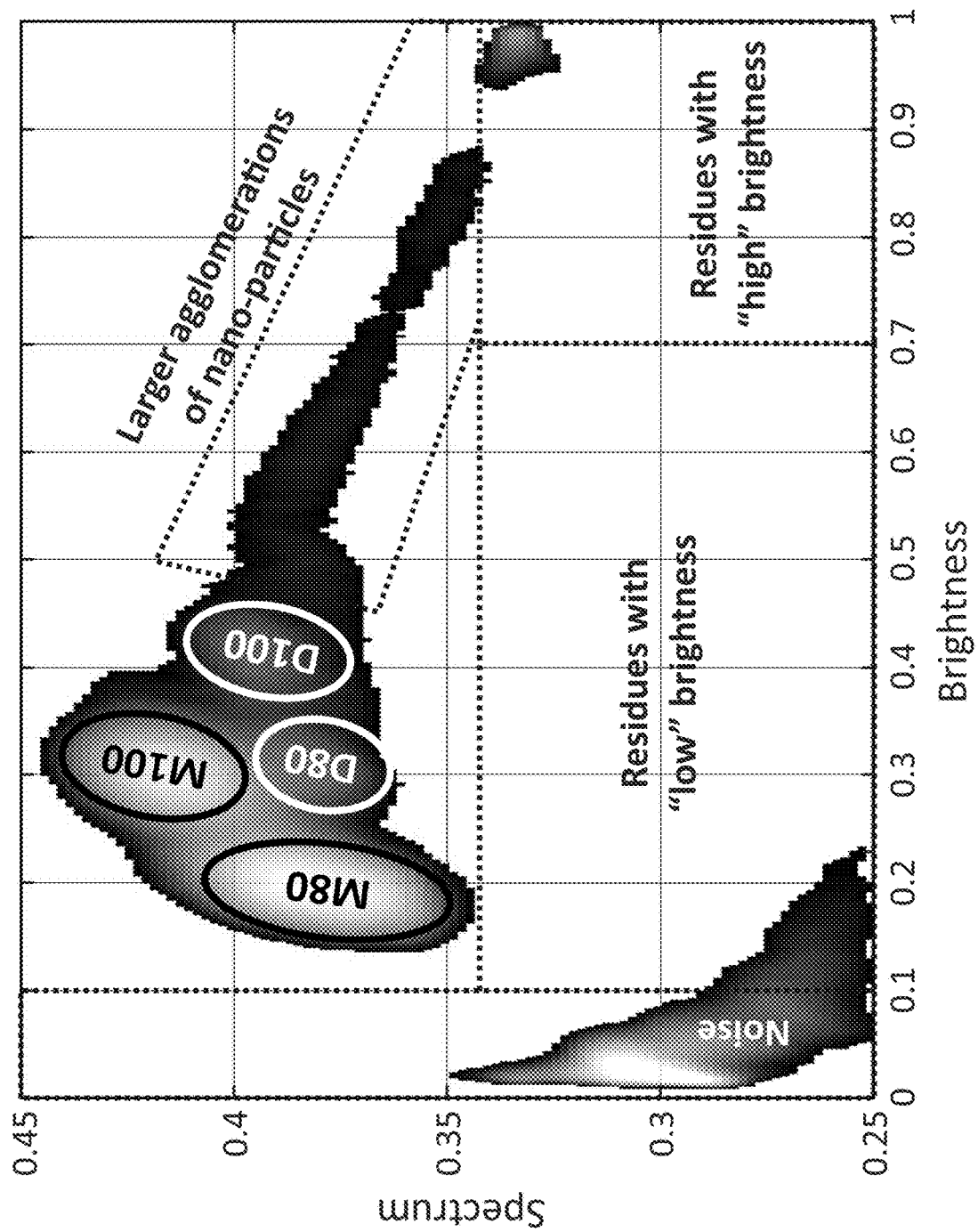
FIG. 11 shows a two-dimensional density distribution of two characterization parameters, brightness and spectrum, for the detection of two biomarkers on a 96-wells biosensor, using gold nano-particles with diameters of 100 nm and 80 nm.

From the characteristics obtained in the previous step, the normalized brightness and one color component were chosen to calculate a 2-dimensional histogram based on all particles found. This 2D histogram, (red normalized) spectrum vs brightness, is shown in FIG. 11. The monomers and dimers of both types (diameters 80 and 100 nm) of GNPs can be easily distinguished: The two most prominent "peaks" correspond to the monomers of particles with 80 nm (M80) and monomers of particles with 100 nm (M100). The corresponding dimers (D80, D100) can also be easily distinguished, while the larger agglomerations overlap substantially. At low brightness values (<0.1), the particles classified as "noise" can be seen. Residues from the fabrication can be distinguished due to their different emission spectrum (<0.33); according to their brightness they are classified in two classes: low for brightness in the range of 0.1-0.7; high for higher brightness values (>0.7).

Based on this histogram, the classification rules are defined. As can be seen in FIG. 11, in this case, the rules correspond to rectangular (noise, residues), elliptical (monomers, dimers), and polygonal regions (agglomerations) of the 2D histogram.

The classification rules were applied to the results from the characterization step, such that the particle class was added to the already known characteristics of each particle found.

Particle Counting

Based on the classification obtained in the previous step, the particles within each class are counted in each image. The result can be visualized as a table with one row per image, and one column per particle class, as Table 4 illustrates bellow.

the biosensor, and the remaining 9×9=81 images are within the sensitive area and used to calculate the principal result of this well: a mean value plus its coefficient of variation, CV. In this experiment, the mean number of particles was calculated after application of a trimming of 40% to the 81 images. The results of all 96 wells on the biosensor for both biomarkers are shown in Table 5 below.

TABLE 5

| Sample | IL-10 | | IL-6 | |
|---|---|---|---|---|
| ID (well) | Count | CV [%] | Count | CV [%] |
| 1 | 112.0 | 14.6 | 54.5 | <u>28.0</u> |
| 2 | 104.5 | 14.8 | 47.3 | *22.7* |
| 3 | 111.6 | 20.4 | 46.7 | <u>30.7</u> |
| 4 | 121.2 | 16.2 | 65.5 | <u>30.2</u> |
| 5 | 142.5 | 18.9 | 79.0 | 19.2 |
| ... | ... | ... | ... | ... |
| 92 | 1800.0 | 10.0 | 974.1 | 15.5 |
| 93 | 1818.4 | 11.4 | 1017.8 | 16.3 |
| 94 | 1935.1 | 15.4 | 966.3 | 17.0 |
| 95 | 1828.6 | 9.6 | 985.9 | 17.5 |
| 96 | 1869.0 | 9.2 | 1039.4 | 13.0 |

Table 5 illustrates the analysis results of the biosensor for the 96 wells. For each well (=sample), the particle counts for the two biomarkers, IL-6 and IL-10, are shown. For each

TABLE 4

| well | image | % sat. | found | class_1 | class_2 | class_3 | class_4 | class_5 | class_6 | class_7 | class_8 |
|---|---|---|---|---|---|---|---|---|---|---|---|
| 1 | 1 | 0.031595 | 191 | 167 | 20 | 4 | 0 | 0 | 0 | 0 | 1 |
| 1 | 2 | 0.030043 | 238 | 223 | 14 | 1 | 0 | 0 | 0 | 0 | 1 |
| ... | | | | | | | | | | | |
| 1 | 169 | 0.036349 | 168 | 152 | 10 | 1 | 1 | 0 | 0 | 0 | 1 |
| 2 | 1 | 0 | 191 | 181 | 10 | 0 | 0 | 0 | 0 | 0 | 0 |
| 2 | 2 | 0.51652 | 213 | 173 | 36 | 8 | 0 | 0 | 1 | 0 | 8 |
| ... | | | | | | | | | | | |
| 96 | 15 | 0.43681 | 1071 | 784 | 191 | 10 | 37 | 19 | 7 | 3 | 7 |
| 96 | 16 | 0.77326 | 1334 | 730 | 711 | 30 | 143 | 63 | 36 | 31 | 21 |
| 96 | 17 | 0.67456 | 1329 | 771 | 203 | 27 | 135 | 63 | 29 | 27 | 18 |
| 96 | 18 | 0.80819 | 1327 | 747 | 198 | 31 | 131 | 67 | 30 | 35 | 22 |
| 96 | 19 | 0.71227 | 1431 | 788 | 212 | 39 | 152 | 80 | 39 | 35 | 22 |
| 96 | 20 | 0.7677 | 637 | 187 | 49 | 27 | 130 | 97 | 29 | 29 | 19 |
| 96 | 21 | 1.3907 | 621 | 202 | 38 | 41 | 149 | 59 | 20 | 27 | 30 |
| 96 | 22 | 0.84234 | 719 | 233 | 43 | 28 | 141 | 96 | 38 | 37 | 25 |
| 96 | 23 | 0.60245 | 646 | 210 | 29 | 20 | 148 | 75 | 37 | 37 | 18 |
| 96 | 24 | 0.71615 | 622 | 251 | 56 | 36 | 109 | 77 | 17 | 22 | 24 |
| 96 | 25 | 0.58621 | 411 | 277 | 39 | 28 | 30 | 11 | 7 | 15 | 17 |
| ... | | | | | | | | | | | |
| 96 | 169 | 0.046536 | 186 | 174 | 12 | 1 | 0 | 0 | 0 | 0 | 1 |

Table 4 illustrates results from the particle counting. Each row corresponds to one image, identified with well and image index. The further columns state the percentage of the image area that appears saturated in brightness, the total number of particles found, and the number per particle class (here, classes 1 . . . 8).

The results per particle class can also be visualized as "heatmaps", i.e., the particle numbers are shown as color-coded or gray-scale images represented in two dimensions/axes that resemble the positions on the biosensor. As an example, FIG. 12 shows the results for one particle class as such a gray-scale heatmap.

Analysis Result

Figure 12:
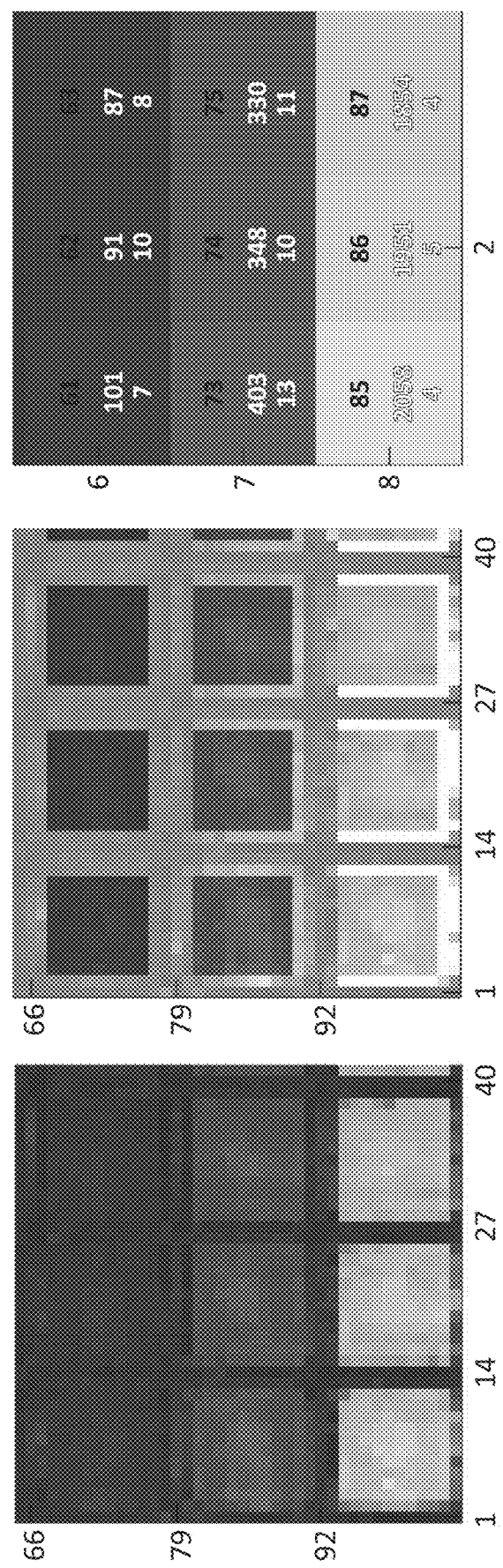
FIG. 12 shows a heatmap in which the analysis results for one particle class are represented in two dimensions that resemble the positions of the samples on the biosensor and the particle numbers are gray-coded.

Typically more than one image is taken per well to improve the counting statistics, in this experiment 13×13 images, as shown in FIG. 12. Here, the outer two rows and columns of images of a well are within non-sensitive area of counting result, the corresponding coefficient of variation is given. To facilitate a first quality control of the measurement, the CVs are displayed in bold (<20%), italics (<25%), or underlined (>25%) font, depending on the degree of variation.

Once a calibration curve has been obtained which relates the number of, e.g., monomers of one type of GNP with the concentration of the biomarker of interest in the sample, the particle counts can be converted into biomarker concentrations (e.g., "12 pg/ml").

Note that in this text, the term "comprises" and its derivations (such as "comprising", etc.) should not be understood in an excluding sense, that is, these terms should not be interpreted as excluding the possibility that what is described and defined may include further elements, steps, etc.

The invention claimed is:

1. Method for optically detecting biomarkers in a biosensor, comprising:
   simultaneously acquiring (1100) spatially and spectrally resolved images from at least one sample of the biosensor with an optical scanner and performing an image analysis (1000) in parallel to the image acquisition (1100);
   wherein the image analysis (1000) comprises:
   reading (2100) data of each acquired image from storage means;
   correcting (2200) the read data to reduce inhomogeneities and noise of each acquired image;
   localizing (2300) particles in each acquired image using the corrected data to obtain a position for each particle;
   characterizing (2400) each particle individually to obtain an intermediate analysis result (5400) which comprises the position and characterization parameters for each particle;
   classifying (2500) the particles based on the characterization parameters of each particle to obtain classification groups of particles;
   counting (2600) a number of particles per classification group for each acquired image;
   controlling (2700) at least a quality value of the intermediate analysis result (5400) obtained by the image analysis (1000) and at least a quality value of each acquired image; and
   calculating an overall analysis result (2800) which comprises at least one statistical value, which is calculated for each biomarker in each sample of the biosensor using the number of particles per classification group for all the images acquired from the same sample, wherein the at least one statistical value per sample is correlated with an indication of the presence of a biomarker in the sample and the controlled quality values are used to correlate with the at least one statistical value calculated per sample for the overall analysis result (2800).

2. Method according to claim 1, further comprising using the overall analysis result (2800) to control the optical scanner for the image acquisition (1100).

3. Method according to claim 2, wherein the optical scanner acquires (1100) images from the sample until the controlled quality values equal or exceed a target value.

4. Method according to claim 1, wherein simultaneously acquiring (1100) spatially and spectrally resolved images comprises:
   illuminating the biosensor at glazing angle with a broadband continuous spectrum;
   capturing scattered light from the at least one sample;
   focusing a surface of the biosensor onto an optical sensor using an auto-focus system;
   producing, with a motorization unit, a movement of the optical scanner in three spatial coordinates, wherein the movement of the optical scanner is relative with respect to the at least one sample of the biosensor.

5. Method according to claim 1, wherein the overall analysis result (2800) per sample and for each biomarker further comprises a concentration of the biomarker.

6. Method according to claim 1, wherein the overall analysis result (2800) further comprises an estimation of an uncertainty of the calculated statistical value.

7. Method according to claim 1, wherein correcting (2200) the read data of each acquired image comprises:
   a background correction (3100) to adjust a black level of the acquired image,
   correcting inhomogeneities (3200) of the brightness and/or color of the acquired image,
   modifying the gamma curve (3300) of the acquired image,
   smoothing (3400) the acquired image to reduce noise of the acquired image.

8. Method according to claim 1, wherein localizing (2300) particles in each acquired image comprises:
   generating at least one test pattern (4100) which represents a particle shape,
   calculating a cross-correlation image (4200) between the brightness and/or color of the acquired image and the generated test pattern,
   defining a mask (4300) for the acquired image based on the calculated cross-correlation image (4200),
   generating a grayscale mask (4400) using the previous defined mask (4300) and the cross-correlation image (4200),
   obtaining the position for each particle by localizing local maxima in the grayscale mask (4400).

9. Method according to claim 1, wherein characterizing (2400) particles comprises:
   obtaining a plurality of smoothed parameters (5100) of the brightness and/or color of each particle,
   evaluating (5200) the plurality of smoothed parameters (5100) at the obtained position of each particle to obtain mean values of the plurality of smoothed parameters (5100),
   obtaining parameters of additional characteristics (5300) of each particle, the parameters selected from at least particle size, particle shape, particle density and spectral characteristics of the particle;
   obtaining the characterization parameters of the intermediate analysis result (5400) as the mean values of the plurality of smoothed parameters (5100) and the parameters of the additional characteristics (5300).

10. Method according to claim 1, wherein classifying (2500) the particles comprises:
    defining the classification groups of the particles (6200) based on the characterization parameters, and, in case of multiplexing (6300) a plurality of biomarkers, defining additional classification groups to account for all the particles used in particle counting (2600),
    defining classification parameters and rules (6400) by mapping combinations of the characterization parameters into each of the defined classification groups and defined additional classification groups,
    performing a segmentation (6500) of a classification parameter space to obtain (6700), for each acquired image, the classification group to which each particle localized in the acquired image belongs.

11. Method according to claim 10, wherein classifying (2500) the particles further comprises excluding the particles (6100) from the particle counting (2600) based on the characterization parameters.

12. Method according to claim 1, wherein the counting (2600) of the particles is weighted with at least one of the characterization parameters.

13. Method according to claim 1, wherein reading (2100) data of the acquired images comprises accessing a memory of a computer in which the image analysis (1000) is running, the computer controlling the optical scanner for acquiring (1100) the images.

14. Method according to claim 1, wherein reading (2100) data of the acquired images comprises accessing at least one storage device of a network with one or more computers in which the image analysis (1000) is running, and the optical scanner being controlled by another computer for acquiring (1100) the images different from any of the computers in which the image analysis (1000) is running.

15. Method according to claim 1, wherein the image analysis (1000) is split between multiple computers of a network, each computer running the image analysis (1000) for a subset of images acquired (1100) by the optical scanner.

16. Method according to claim 1, wherein the image analysis (1000) is performed sequentially by at least one computer, the at least one computer analyzing one image per time, or the image analysis (1000) is performed in parallel by the at least one computer, the at least one computer analyzing multiple images per time.

* * * * *